(12) United States Patent
Gonzalez-Hernandez (10) Patent No.: US 8,343,197 B2
(45) Date of Patent: Jan. 1, 2013

(54) CURVED ASSEMBLY FOR REATTACHMENT OF FRAGMENTED BONE SEGMENTS

(75) Inventor: Eduardo Gonzalez-Hernandez, Coconut Grove, FL (US)

(73) Assignee: Toby Orthopaedics, Inc., Coral Gables, FL (US)

(*) Notice: Subject to any disclaimer, the term of this patent is extended or adjusted under 35 U.S.C. 154(b) by 1122 days.

(21) Appl. No.: 12/101,508

(22) Filed: Apr. 11, 2008

(65) Prior Publication Data

US 2009/0118771 A1    May 7, 2009

Related U.S. Application Data

(66) Substitute for application No. 60/922,651, filed on Apr. 11, 2007.

(51) Int. Cl.
    *A61B 17/80*     (2006.01)

(52) U.S. Cl. .......................................... 606/286; 606/304

(58) Field of Classification Search .......... 606/300–321, 606/79, 80; 411/392, 395
See application file for complete search history.

(56) References Cited

U.S. PATENT DOCUMENTS

| | | | |
|---|---|---|---|
| 4,175,555 A | | 11/1979 | Herbert |
| 4,716,893 A | * | 1/1988 | Fischer et al. ................. 606/66 |
| 4,723,541 A | * | 2/1988 | Reese ........................... 606/916 |
| 4,940,467 A | * | 7/1990 | Tronzo ............................ 606/66 |
| 4,959,064 A | * | 9/1990 | Engelhardt ..................... 606/65 |
| 5,562,672 A | | 10/1996 | Huebner |
| 5,964,768 A | | 10/1999 | Huebner |
| 6,080,162 A | | 6/2000 | Dye et al. |
| 6,955,513 B2 | * | 10/2005 | Niku ............................. 411/382 |
| 7,582,107 B2 | * | 9/2009 | Trail et al. ..................... 606/304 |
| 2002/0045903 A1 | | 4/2002 | Bonutti |
| 2002/0090999 A1 | * | 7/2002 | Romano ......................... 464/58 |
| 2004/0210227 A1 | * | 10/2004 | Trail et al. ....................... 606/73 |
| 2004/0220577 A1 | * | 11/2004 | Cragg et al. .................... 606/80 |
| 2005/0197660 A1 | * | 9/2005 | Haid et al. ...................... 606/61 |
| 2005/0267481 A1 | | 12/2005 | Carl et al. |
| 2006/0084992 A1 | | 4/2006 | Michelson |
| 2008/0177333 A1 | * | 7/2008 | Ferguson ...................... 606/304 |
| 2008/0188854 A1 | * | 8/2008 | Moser ............................ 606/80 |

* cited by examiner

*Primary Examiner* — Kevin T Truong
*Assistant Examiner* — Michael Araj (57) ABSTRACT

The present invention is comprised generally of a curved assembly for use in reattaching bone segments created by fracture or for mating bone fragments in other reconstructive procedures. The present invention further comprises a curved drill to create the hole into which the curved screw is attached. Preferably, the curved screw and drill of the present invention are designed such that they can be used singularly or in combination with a bone plate to support bone fragments and prevent them from moving with respect to the plate.

2 Claims, 7 Drawing Sheets

CURVED ASSEMBLY FOR REATTACHMENT OF FRAGMENTED BONE SEGMENTS

CROSS REFERENCES TO RELATED APPLICATIONS

This application claims the benefit under 35 U.S.C. §119(e) of U.S. Provisional Application No. 60/922,651, filed on Apr. 11, 2007, the complete disclosure of which is incorporated herein by reference in its entirety.

FIELD OF THE INVENTION

The present invention relates to orthopedic bone screws and drills used in the reattachment of fragmented bone segments.

BACKGROUND OF THE INVENTION

The present device and method provides a significant departure from straight screws for fixation of bone or other solid material.

Traditional screws are basically solid devices with a head that articulates with a screwdriver, a straight shaft, and a tip. The shaft may be fully threaded or only partially threaded; a portion of the tip may be threaded and may or may not have a self drilling or self tapping design. In addition, the head of the screw itself may have threads that articulate with a metal plate to assist the screw in locking to the plate.

The clinical success of plate and screw systems for internal fixation of fractures is well documented. When used in conjunction with a bone plate, a conventional screw would enter into a smooth aperture in the plate and is then driven into the bone. The head of the screw would then apply a downward pressure on the plate, assuming the head of the screw is larger than the aperture in the plate.

Recent advances in the field of orthopedic fracture fixation have led to the development of "locking" plates. In the locking configuration the screw head itself is threaded. The corresponding aperture in the plate is compatibly threaded. When the screw has been driven sufficiently into the bone, the head of the screw can engage the corresponding threads on the plate and create a locked assembly, thus providing a desirable mechanical advantage over conventional plating systems.

Screws are frequently used by themselves in bone fracture and reconstructive procedures. There are many bones in the human skeleton that are constituted largely of cancellous "spongy" bone. Often, these bones are best fixed with a screw that can be entirely buried into the substance of the bone without leaving any component of the screw outside to minimize irritating adjacent tissues, or to avoid scouring the cartilage of a joint. In such cases, it is desirable that the head of the screw itself has threads designed to engage bone, i.e. "bone threads."

Another option for fixation of cancellous bone fractures is, what is referred to by those skilled in the art, as a "headless screw." As the name implies, a headless screw has no distinctive head. The screw driver engages the screw at the terminus away from the tip or leading end of the screw. The scaphoid bone in the wrist is often fixed with such headless screws, or screws that can be buried entirely into the bone. Presently, there are several known screws in the art designed for use with scaphoid bones and other similar bones. For example, the Herbert screw (U.S. Pat. No. 4,175,555, issued to Herbert); the Accutract screw from Acumed (U.S. Pat. Nos. 5,562,672 and 5,964,768, issued to Huebner); the TwinFix screw from Stryker-Leibinger; the Kompressor screw from KMI; and the SLIC screw system from Acumed.

All of these screws are straight, except for the SLIC screw, which is articulated at the waist. Most existing screws also have a cannulated version for increased accuracy of insertion. A smooth pin can also act as a guide by first inserting the pin into the bone under radiographic control.

The scaphoid bone has an elongated curved shape that makes it difficult to fix with a straight screw. Frequently, the screw is placed in a suboptimal position and fails to engage and hold the fractured bone segments. The challenge in scaphoid fracture fixation is placing a straight screw into a curved bone. Failure to achieve accurate placement of the screw into the bone can lead to failure of fracture healing.

It is therefore an object of the present invention to improve bone fracture fixation and facilitate placement of a bone screw. It is a further object of the present invention to provide a curved screw that can follow the natural curvature of any skeletal bone, especially fractured joints such as found in the shoulders, wrists, and equivalents thereof. It is another object of the present an invention to provide a curved apparatus that operates in conjunction with a curved screw as well as a curved drill bit capable of various lengths and curvatures. It is a further object of the present invention to provide a curved screw capable of compressively attaching to a bone plate. It is a further object of the present invention to provide a curved drill bit and curved screw that can be used in conjunction to facilitate reattachment of fractured bone segments.

SUMMARY OF THE INVENTION

The present invention generally comprises a curved assembly having an inner shaft or core, a sleeve, a proximal end, and a distal end capable of respectively attaching a screw head or drill bit drive access and a screw tip or drill bit.

In one embodiment of the present invention, the sleeve is comprised of a rigid material that encases an inner member comprised of a flexible inner drive shaft that connects the head and tip of a screw, or, in another embodiment, a flexible drive shaft that connects a drill bit and drill bit drive access.

In another embodiment of the present invention, the curved assembly the inner member is comprised of a rigid core, either hollow or solid, and a sleeve comprises a flexible material that connects the head to the tip of the screw, or, in another embodiment, a flexible sleeve that connects a drill bit and drill bit drive access.

In another embodiment of the present invention, the flexible sleeve with screw tip and screw head is externally threaded. The threaded sleeve is preferably made of a spiral thread that articulates with multiple rings, preferably at regular intervals on the thread to prevent unraveling of the thread when the screw tip and screw head are advanced. The rings that hold the spiral thread to the rigid curved shaft, while free to rotate, can be kept from sliding along the curved shaft by features along the shaft such as snap rings or other prominences. In a preferred embodiment, a freely rotating ring alternates with a snap-ring. In this manner, the transfer of the driving thrust of the spiral thread is more uniform at every snap ring or prominence holding the rings of the thread, and not only at the head of the screw. Thus holding the rings that stabilize the thread in the same position along the curved assembly improves the mechanical performance of the device and approximates the articulated curved screw as much as possible to a straight screw. In addition, when the screw is backed out, the tendency of the spiral thread to compress and bind on the shaft is nullified by the rings that stabilize the thread to the shaft. In this embodiment, the screw could be removed in a delayed fashion without concern for bone building up along the shaft in between the head and the tip of the screw.

In yet another embodiment of the present invention, the curved assembly comprises a hollow rigid sleeve encasing a hollow or solid flexible drive shaft, wherein said flexible drive shaft connects the head of the screw with the tip of the screw. The curved assembly has another component comprised of a flexible sleeve which is externally threaded. The flexible sleeve would also connect the head of the screw with the tip of the screw. In this embodiment, the head of the screw is driven via the flexible shaft and not the outer flexible threaded sleeve. Torque transfer from the head of the screw to the tip of the screw takes place through the flexible drive shaft minimizing the tendency of the threaded sleeve to unravel.

DETAILED DESCRIPTION OF THE PREFERRED EMBODIMENTS

Figure 1:
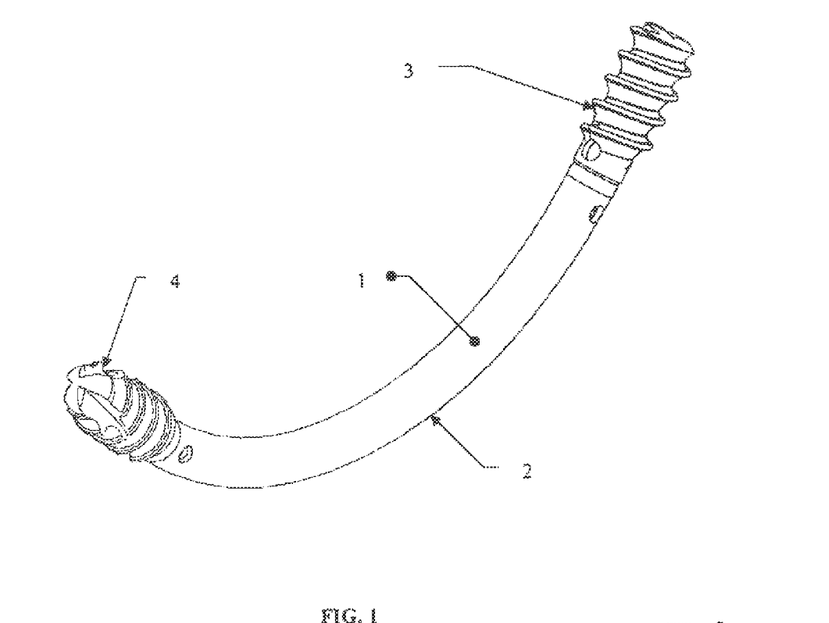
FIG. 1 illustrates a perspective view of the curved assembly having a rigid curved sleeve with a screw head and screw tip attached to the proximal and distal ends of the assembly.

FIG. 1, depicts a curved assembly 1 comprised of a curved sleeve 2 with a proximally attached screw head 3 and a distally attached screw tip 4. In one embodiment of the present invention, the curved sleeve 1 is rigid, and can be made of any implantable material used by those of ordinary skill in the art, including but not limited to titanium alloys or stainless steels. In this embodiment, the rigid sleeve determines the curvature of the curved assembly.

Figure 2:
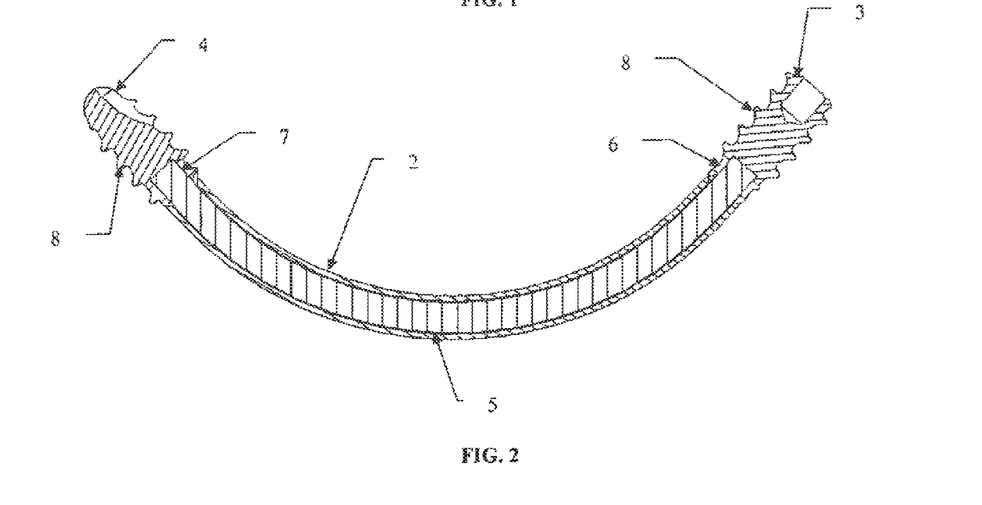
FIG. 2 illustrates a cross-sectional view of the curved assembly having a rigid curved sleeve, a flexible inner drive shaft, and a screw head and screw tip attached to the proximal and distal ends of the assembly.

The inner portion of curved sleeve is hollow and shaped to encase an inner member. As illustrated by FIG. 2, inner member is comprised of a drive shaft 5. The drive shaft 5 comprises a first proximal end 6 attached to a screw head 3 and a second distal end 7 attached to a screw tip 4. In one embodiment of the present invention, the drive shaft 5 is flexible, can be hollow or solid, and can be made of any implantable material used by those of ordinary skill in the art.

As illustrated by FIG. 2, the flexible drive shaft 5 is encased by the hollow portion of the rigid curved sleeve 2. Screw head 3 attaches to the flexible drive shaft's first proximal end, and screw tip attaches to the flexible drive shaft's second distal end. Attachment of the screw head and screw tip to the proximal and distal ends of the drive shaft can be made by any method known by one of ordinary skill in the art, such as, for example, laser welding or any equivalent thereof.

In a preferred embodiment of the present invention, screw head and screw tip each have external screw threads 8. The diameter of the screw head is preferably larger than the diameter for the outer portion of the curved sleeve. The diameter of the screw tip is also preferably larger than the diameter for the outer portion of the curved sleeve.

Figure 3:
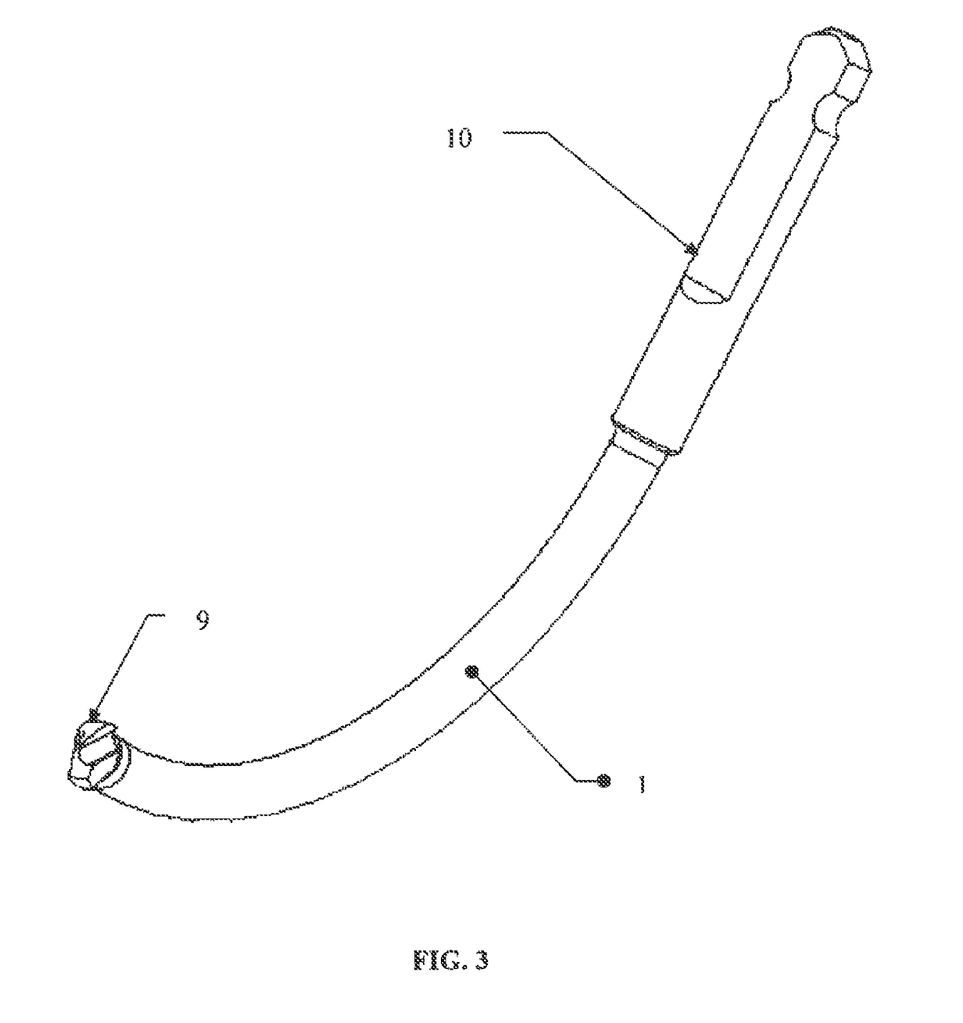
FIG. 3 illustrates a perspective view of the curved assembly having a rigid curved sleeve with a drill bit and drill bit drive access attached to the proximal and distal ends of the assembly.

As illustrated in FIG. 3, in another embodiment of the present invention, a drill bit 9 attaches to the flexible drive shaft's 5 first distal end, and drill bit drive access 10 attaches to the drive shaft's second proximal end. Attachment of the drill bit and drill bit drive access to the proximal and distal ends of the drive shaft can be made by any method known by one of ordinary skill in the art, such as, for example, laser welding or any equivalent thereof. The diameter of the drill bit or drill bit drive access is preferably larger than the diameter of the outer portion of the curved sleeve.

Figure 5:
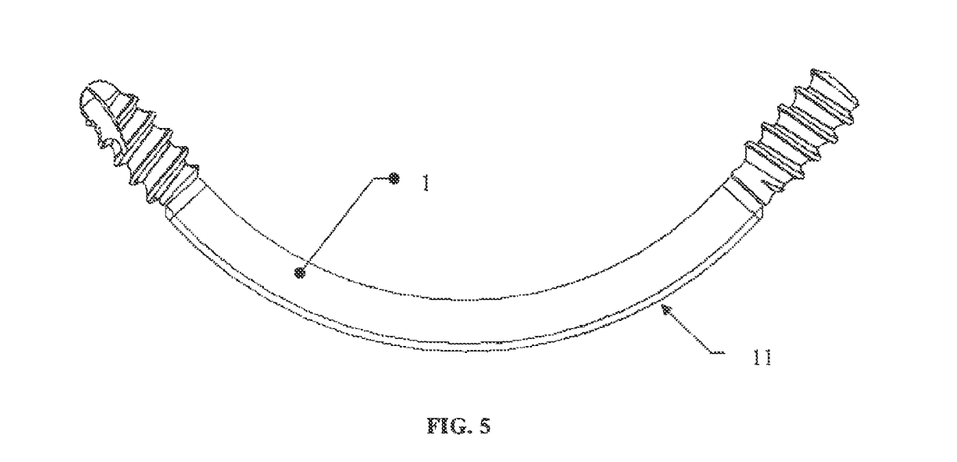
FIG. 5 illustrates a side view of the curved assembly's rigid curved sleeve with an outwardly radiating ridge.
Figure 6:
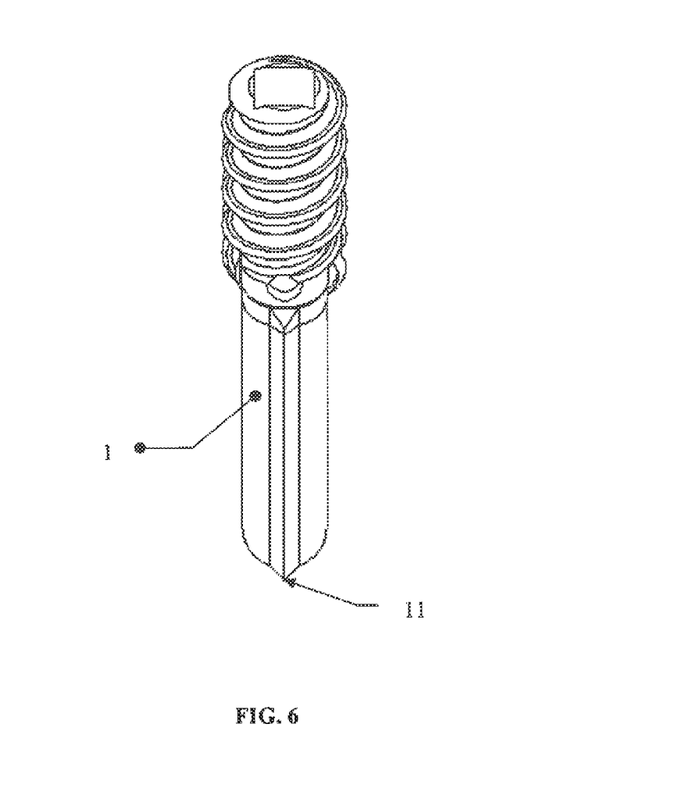
FIG. 6 illustrates a rear view of the curved assembly's rigid curved sleeve with an outwardly radiating ridge.

The outer surface of the curved sleeve may be smooth, or, as depicted in FIGS. 5 & 6, in another embodiment, may be further comprised of one or more outwardly radiating ridges 11 which help improve fixation into the surrounding bone.

Figure 7:
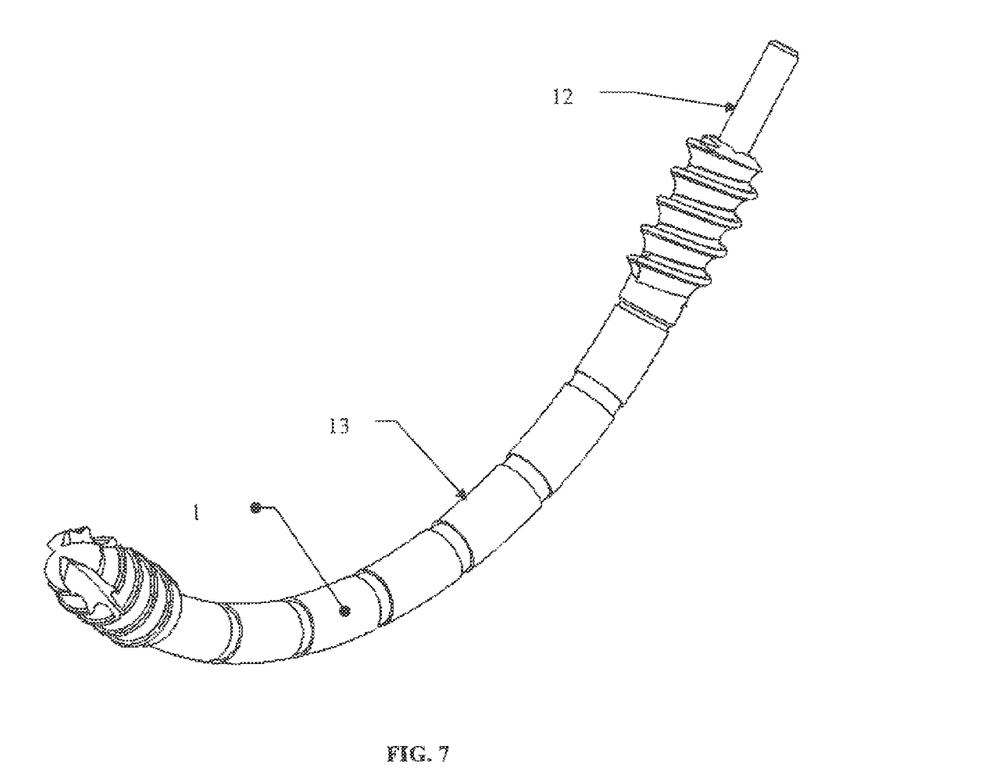
FIG. 7 illustrates a perspective view of the curved assembly having a flexible curved sleeve with a screw head and screw tip attached to the proximal and distal ends of the assembly.
Figure 8:
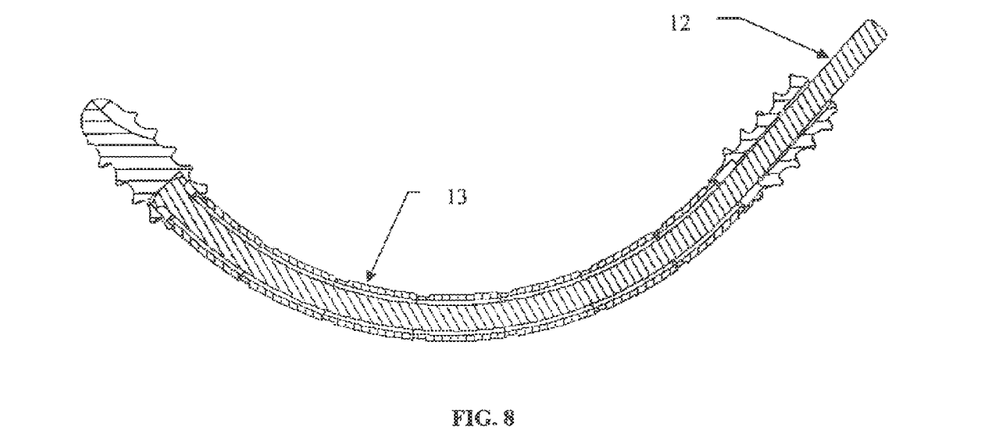
FIG. 8 illustrates a cross-sectional view of the curved assembly having a flexible curved sleeve, a rigid inner portion, and a screw head and screw tip attached to the proximal and distal ends of the assembly.

As depicted in FIGS. 7 & 8, in another embodiment of the present invention, the inner portion of the curved assembly is comprised of a solid rigid core 12. The curvature of the rigid core determines the curvature of the curved assembly. A flexible sleeve 13 is fitted over the rigid core. The flexible curved sleeve 13 is capable of turning freely on the surface of the rigid core 12. In another embodiment of the present invention, the flexible sleeve is attached to a screw head at its first proximal end, and attached to a screw tip at its second distal end. The diameter of the screw head and tip are preferably larger than the diameter of the curved sleeve. As the screw head is turned, either manually or with an auxiliary power source, the flexible sleeve transfers torque to the screw tip. In this embodiment, the rigid core remains stationary, and preferably engages to the inner portion of an articulated driver to prevent precession of the screw itself, while the outer portion of the articulated driver transfers torque to the head of the screw.

In another embodiment of the present invention, the flexible sleeve is attached to a drill bit at its first distal end, and attached to a drill bit drive access at its second proximal end. The diameters of the drill bit and drill bit drive access are preferably larger than the diameter of the flexible curved sleeve. As the proximal end of the drill is driven by hand or auxiliary power source, the flexible sleeve then transfers the torque to the drill bit.

Figure 9:
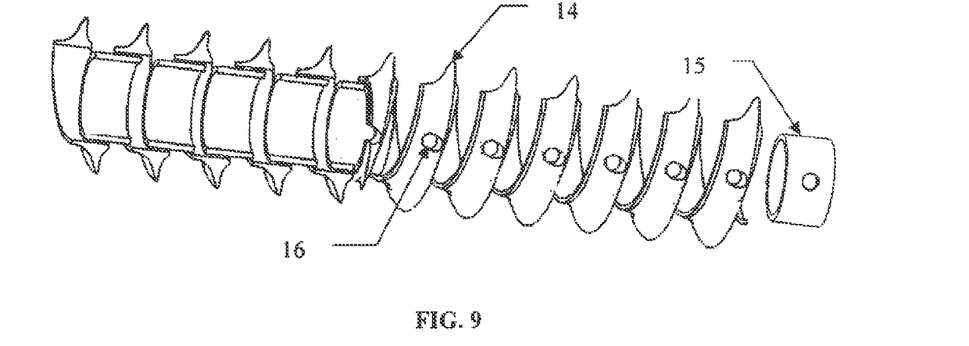
FIG. 9 illustrates a close-up view of the curved assembly's flexible curved sleeve with external threading and rings.

As depicted in FIG. 9, in another embodiment of the present invention, the flexible sleeve is externally threaded 14. The threaded sleeve is preferably made of a spiral thread that articulates with a plurality of rings 15, preferably equally spaced on the thread to prevent unraveling of the thread when the curved assembly is advanced. As depicted in FIG. 9, each individual ring 15 holds the thread to the rigid curved core and minimizes the possibility of unraveling of the thread. The thread and the rings articulate via a single peg 16 which is wider at its ends than its shaft and is positioned to maintain the spiral thread 14 in close relationship to the ring 15 and to the curved inner member. In another embodiment of the present invention, ring 15 is further comprised of a locking mechanism, such as, for example, a pin and aperture that snap together along the circumference of the ring to prevent the ring from freely rotating around the curved inner member. In yet another embodiment, rings 15 with and without a locking mechanism are alternated along the surface of the curved inner member.

Figure 10:
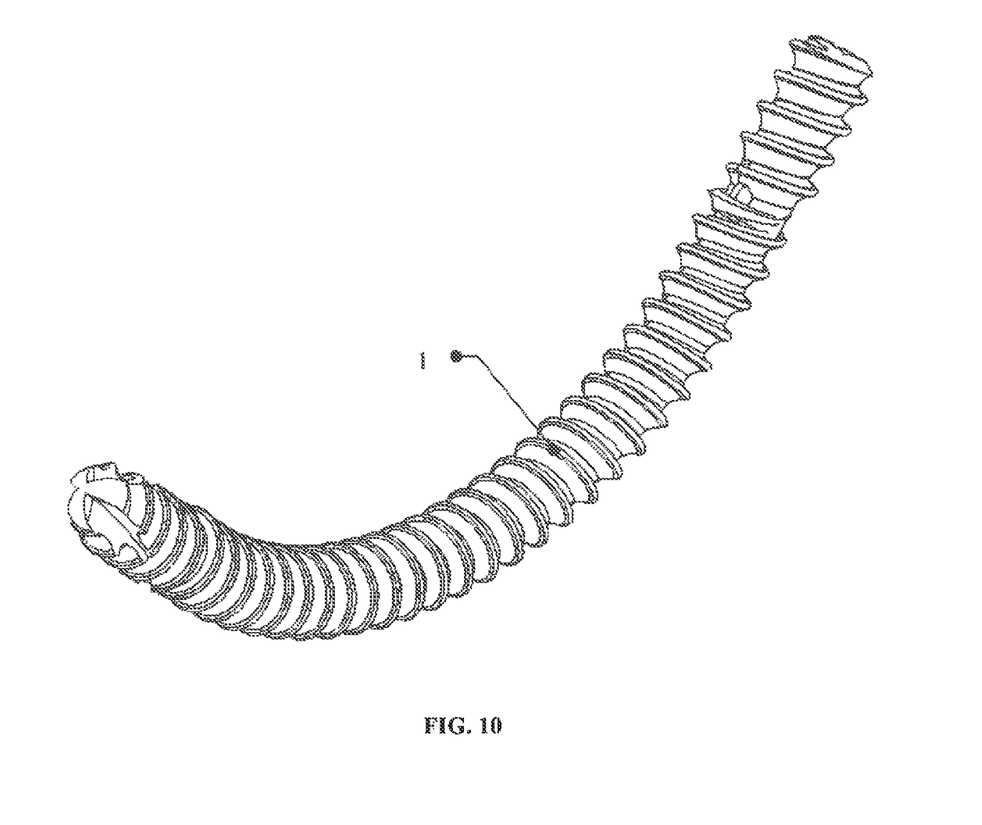
FIG. 10 illustrates a perspective view of the curved assembly's flexible curved sleeve with external threading with rigid inner sleeve and flexible inner drive shaft.
Figure 11:
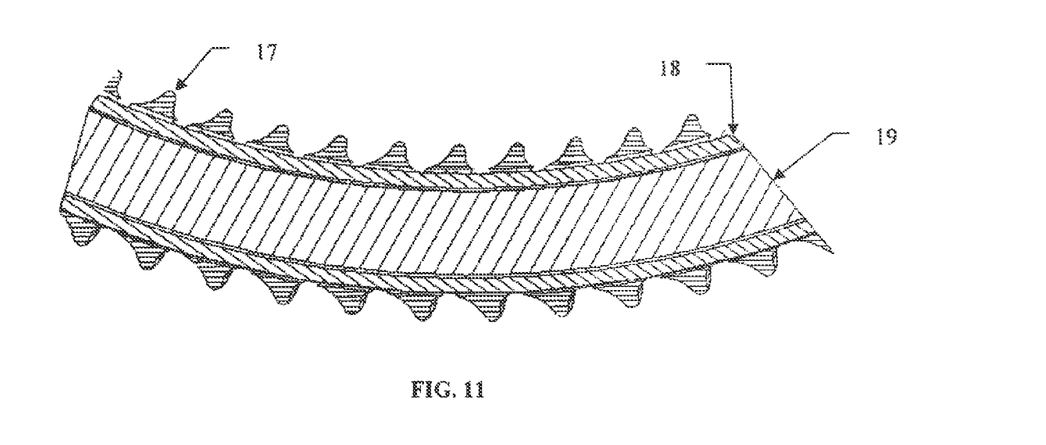
FIG. 11 illustrates a cross-sectional view of the curved assembly's flexible curved sleeve with external threading with rigid inner sleeve and flexible inner drive shaft.

As depicted in FIGS. 10 & 11, in another embodiment of the present invention, the curved assembly is comprised of an outer flexible threaded sleeve 17 with a proximal end, and a distal end, and can be made of any implantable material used by those of ordinary skill in the art, including but not limited to titanium alloys or stainless steels. The flexible shaft comprises a first proximal end connected to a screw head and a second distal end connected to a screw tip. The rigid inner sleeve 18 determines the curvature of the screw. The inner portion of curved sleeve is preferably hollow and preferably shaped to encase a drive shaft. The drive shaft comprises a first proximal end connected to a screw head and a second distal end connected to a screw tip. In this embodiment of the present invention, the drive shaft 19 is flexible, and can be made of any implantable material used by those of ordinary skill in the art.

The flexible drive shaft 19 is encased by the rigid curved sleeve. Screw head attaches to the drive shaft's first proximal end, and screw tip attaches to the drive shaft's second distal end. Attachment of the screw head and screw tip to the proximal and distal ends of the drive shaft can be made by any method known by one of ordinary skill in the art, such as, for example, laser welding or any equivalent thereof.

Several embodiments of the present invention can be used in conjunction. For example, the curved assembly with proximally and distally attached drill bit and drill bit drive access can be introduced into a bone through a suitable drill guide. The drill guide can be attached to a bone plate or, alternatively, drilled freely, with the aid of a hand held curved guide into the bone fragments to be attached. The curved assembly with proximally and distally attached screw head and tip can then be inserted into the pre-drilled hole until the first proximal end meshes with a mating threaded hole in the bone plate or, alternatively, into the bone freely without a plate.

Figure 4:
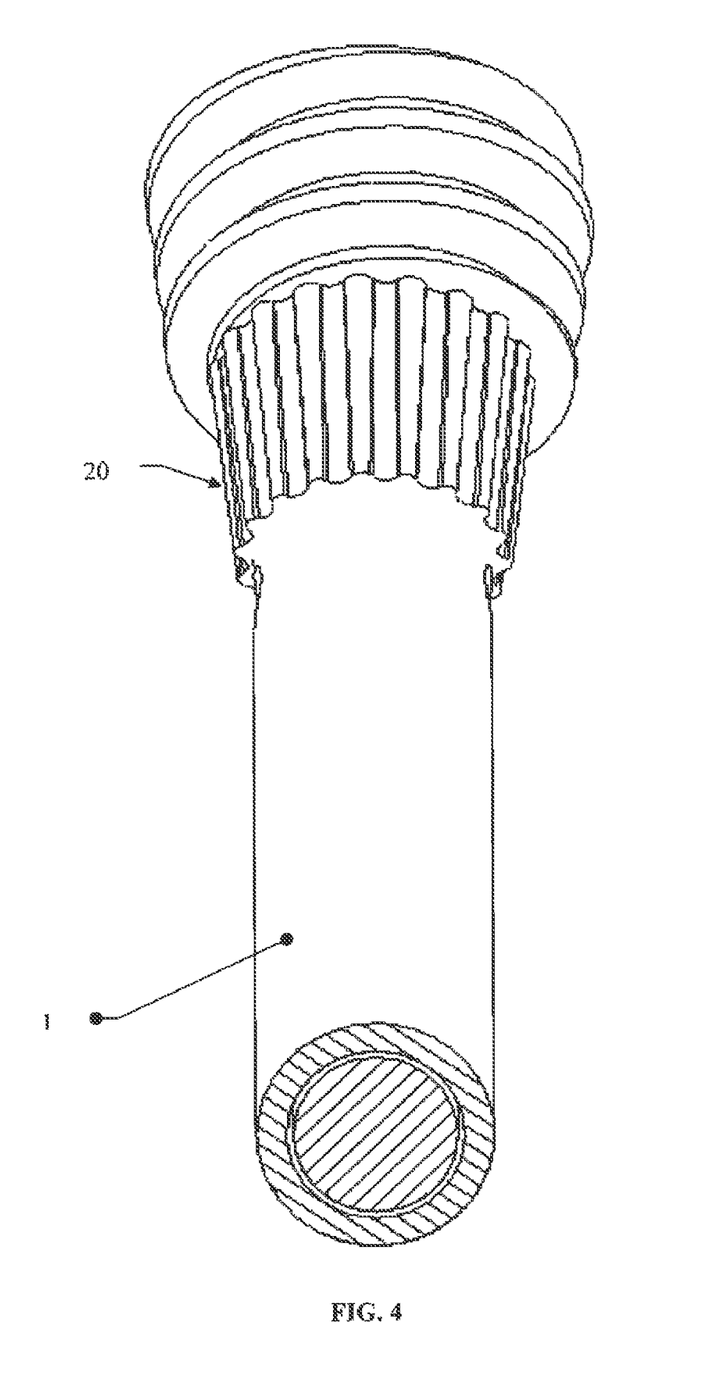
FIG. 4 illustrates a close-up view of the proximal end of the curved assembly's flared outer sleeve with splines.

As depicted in FIG. 4, in a further embodiment of the present invention, when the curved assembly with screw head and tip attachments is used in conjunction with a bone plate, the end of the first proximal end of the curved sleeve is preferably flared and splined. The splines 20 of the curved sleeve mate with corresponding grooves in a bone plate. When the head of the screw articulates with the plate, the splines interact with corresponding grooves in the bone plate, thus providing additional rotational rigidity necessary for locking the curved assembly to the plate.

The invention claimed is:

1. A curved assembly for reattachment of fragmented bone segments, the curved assembly comprising:
    a curved inner portion;
    a hollow outer sleeve encasing said curved inner portion, said hollow out sleeve comprising a flexible material, said hollow outer sleeve including a surface comprising external threading, and said external threading comprising a plurality of rings attaching said external threading to said hollow outer sleeve;
    a first proximal end adjacent to one of a screw head or drill bit drive access; and
    a second distal end adjacent to the other of a screw tip or drill bit.

2. The curved assembly of claim 1, wherein said curved inner portion comprises a rigid core.

* * * * *